(12) United States Patent
Schattenmann

(10) Patent No.: US 6,258,971 B1
(45) Date of Patent: Jul. 10, 2001

(54) METHOD FOR MAKING ORGANOOXYSILANES

(75) Inventor: Florian Johannes Schattenmann, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/617,936

(22) Filed: Aug. 17, 2000

(51) Int. Cl.$^7$ ........................................... C07F 7/08
(52) U.S. Cl. ............................. 556/478; 556/482
(58) Field of Search .................... 556/478, 482

(56) References Cited

U.S. PATENT DOCUMENTS 2,473,260    6/1949   Rochow .

FOREIGN PATENT DOCUMENTS 3821483    6/1988   (DE) .

OTHER PUBLICATIONS

"Polymeric Methyl Silicon Oxides", E.G. Rochow and W.F. Gilliam, vol. 63, Mar. 1941, pp. 798–800.

"A Silicate Substitution Route in Organosilicon Compounds", G.B. Goodwin and M.E. Kenney, 1990 American Chemical Society, pp., 251–263.

Abstract, "Preparation of Diorganodialkoxysilanes", Graefe et al., p. 1, Jan. 1998.

Bazant et al., "Organosilicon Compunds", vol. 2, part 1, Academic Press (NY), pp. 109 and 307, 1965.*

* cited by examiner

*Primary Examiner*—Paul F. Shaver
(74) *Attorney, Agent, or Firm*—Bernadette M. Bennett; Noreen C. Johnson

(57) ABSTRACT

A method for the preparation of organooxysilanes containing at least one silicon-carbon bond is provided which comprises reaction of at least one tetraorganooxysilane with at least one metal hydride.

15 Claims, No Drawings

METHOD FOR MAKING ORGANOOXYSILANES

FEDERAL RESEARCH STATEMENT

The United States Government may have certain rights in this invention pursuant to contract number DE-FC02-98CH10931 awarded by the United States Department of Energy.

BACKGROUND OF INVENTION

The present invention relates to a method for making organooxysilanes. More particularly, the present invention relates to a process involving the reaction of a tetraorganooxysilane in the presence of a metal hydride.

Organooxysilanes are silicon-containing compounds of the formula $R_mSi(RO)_n$ where each R independently represents a monovalent hydrocarbon group such as an alkyl group, aryl group, aralkyl groups, alkaryl groups, cycloalkyl groups, or bicycloalkyl groups; "n" is in a range between 1 and 3; "m" is in a range between 1 and 3; and "n+m" is 4. Silicon-containing compounds with silicon-carbon bonds, such as organooxysilanes, are commonly made from silicon dioixide via elemental silicon. Unfortunately, elemental silicon is manufactured from silicon dioxide by an energy intrusive reduction process.

The process commonly used commercially for the production of silicones and more particularly, alkoxysilanes, was first described by Rochow et al., U.S. Pat. No. 2,473,260. The Rochow process uses silicon, also referred to as elemental silicon, as a starting material. To prepare elemental silicon, silicon dioxide must be reduced. The elemental silicon is then oxidized to yield alkoxysilanes via a reaction of the silicon with methanol in the presence of a copper catalyst. It is well known in the art that the silicon-oxygen bond in silicon dioxide is extremely stable. In order to break the silicon-oxygen bond, a large amount of energy is consumed when silicon dioxide is reduced to elemental silicon. Thus, due to the large amount of energy needed to break the silicon-oxygen bond, the synthesis of silicones from silicon dioxide using the Rochow process is expensive and not energy efficient.

In the past, the synthesis of silicon-containing compounds with silicon-carbon bonds has relied heavily on the reduction of silicon dioxide to elemental silicon. Unfortunately, the large amount of energy needed for synthesizing silicones such as organooxysilanes from silicon dioxide can be problematic. Thus, new synthetic routes are constantly being sought which can form silicon-carbon bonds.

SUMMARY OF INVENTION

The present invention provides a method for the preparation of organooxysilanes containing at least one silicon-carbon bond comprising reaction of at least one tetraorganooxysilane with at least one metal hydride.

DETAILED DESCRIPTION

The present invention relates to a process involving the reaction of at least one tetraorganooxysilane and at least one metal hydride to form an organooxysilane containing at least one silicon-carbon bond. Tetraorganooxysilanes are of the formula $(RO)_4Si$ where each R independently represents a monovalent hydrocarbon group such as alkyl groups, aryl groups, aralkyl groups, alkaryl groups, cycloalkyl groups, or bicycloalkyl groups. The term "alkyl group" is intended to designate both normal alkyl and branched alkyl groups. Normal and branched alkyl groups are preferably those containing carbon atoms in a range between about 1 and about 22, and include as illustrative non-limiting examples methyl, ethyl, propyl, isopropyl, butyl, tertiary-butyl, pentyl, neopentyl, hexyl, octyl, decyl, dodecyl. Aryl groups include an example such as phenyl. Cyclo- or bicycloalkyl groups represented are preferably those containing ring carbon atoms in a range between about 3 and about 12 with a total number of carbon atoms less than or equal to about 50. Some illustrative non-limiting examples of cycloalkyl groups include cyclobutyl, cyclopentyl, cyclohexyl, methylcyclohexyl, and cycloheptyl. Preferred aralkyl groups are those containing carbon atoms in a range between about 7 and about 14; these include, but are not limited to, benzyl, phenylbutyl, phenylpropyl, and phenylethyl. Typical tetraorganooxysilanes include tetraalkoxysilanes such as tetramethoxysilane, tetraethoxysilane, and tetraisopropoxysilane; tetraaryloxysilanes such as tetraphenoxysilane; as well as tetra(alkoxyaryloxy)silanes such as dimethoxydiphenoxysilane. Typically, the level of purity of the tetraorganooxysilane is at least about 80% by weight and preferably, about 95% by weight.

Metal hydrides include, but are not limited to, sodium hydride, lithium hydride, potassium hydride, rubidium hydride, cesium hydride, magnesium hydride, calcium hydride, strontium hydride, barium hydride, aluminum hydride, and combinations thereof. The metal hydride is preferably sodium hydride. Metal hydrides also include metal borohydrides, for example, lithium borohydride, potassium borohydride and sodium borohydride. Although the present invention is not dependent upon theory, the presence of hydrogen in the metal hydride may act as a base as well as a nucleophile to promote the formation of the organooxysilane.

Organooxysilanes are compounds of the formula $R_mSi(RO)_n$ where R is defined as above, "n" is in a range between 1 and 3, "m" is in a range between 1 and 3, and "n+m" is 4. Preferably, R is methyl or ethyl, n is 3 and m is 1.

The reaction commonly can be practiced in a fixed bed reactor. The method for preparation of organooxysilanes, however, can be performed in other types of reactors, such as fluid bed reactors and stirred bed reactors. More specifically, the fixed bed reactor is a column that contains the metal hydride wherein a carrier gas, such as an inert gas of hydrogen or argon, is passed through at a rate in a range between about 0.1 milliliters per minute (ml/min) and about 100 ml/min and preferably, in a range between about 0.5 ml/min and about 30 ml/min. The tetraorganooxysilane is typically fed into the carrier gas stream. A stirred bed is similar to a fixed bed in which there is mechanical agitation of some sort in order to keep the bed in constant motion. A fluidized bed reactor, on the other hand, is a bed comprising metal hydride which is fluidized; that is, the metal hydride is suspended in the gas, typically argon, that is passed through the reactor. Reaction typically occurs at a temperature in a range between about 50° C. and about 600° C. and commonly, in a range between about 200° C. and about 450° C.

The reaction of the present invention can be performed in batch mode, continuous mode, or semi-continuous mode. With a batch mode reaction, for instance, all of the reactant components are combined and reacted until most of the reactants are consumed. In order to proceed, the reaction has to be stopped and additional reactant added. A fixed bed and stirred bed may both be run under batch conditions. In contrast, a fluidized reactor is typically run under continuous conditions. With continuous conditions, the reaction does not have to be stopped in order to add more reactants.

The tetraorganooxysilane is typically added to the reactor via any convenient method to provide batch, continuous, or semi-continuous means of addition. A pumping device, such as a motor driven syringe, is an example of a continuous means of addition. A motor driven syringe allows for consistent amounts of tetraorganooxysilane to be added to the reaction mixture at given time intervals. Addition of the tetraorganooxysilane via a motor driven syringe is illustrative and non-limiting. Manual injection is also a common method for the addition of tetraorganooxysilanes. Typically, the tetraorganooxysilane is added at a rate in a range between about 0.1 milliliters per hour (ml/h) and about 10 ml/h, and preferably, in a range between about 0.5 ml/h and about 2.1 ml/h. The tetraorganooxysilane is typically added in a mole ratio of metal hydride to tetraorganooxysilane in a range between about 10:1 and about 1:100 and commonly, a mole ratio of metal hydride to tetraorganooxysilane in a range between about 5:1 and 1:10. The reaction is typically at about atmospheric pressure.

Products in the organooxysilane synthesis may be isolated by any convenient means. Typically, product(s) may be isolated by condensation into fractions typically referred to as condensate. Products may be purified by any convenient means such as distillation. Once the fractions are collected, the formation of the organooxysilane may be confirmed by such methods as gas chromatography (GC), gas chromatography-mass spectroscopy (GC/MS), and proton nuclear magnetic resonance spectroscopy ($^1$H-NMR), carbon nuclear magnetic resonance spectroscopy ($^{13}$C-NMR) and silicon nuclear magnetic resonance spectroscopy ($^{29}$Si-NMR).

An important advantage of using a tetraorganooxysilane and metal hydride as starting materials for the preparation of organooxysilanes with at least one silicon-carbon bond is that it is energy efficient. The present invention does not require the reduction of silicon dioxide to elemental silicon.

Organooxysilanes obtained by the present method may be used in a wide variety of applications. For example, organooxysilanes may be used as precursors to silicones and organofunctional silicon compounds, precursors to pure and ultra-pure silicon dioxide, coupling agents, additives for plastic applications, and adhesion promoters.

In order that those skilled in the art will be better able to practice the invention, the following examples are given by way of illustration and not by way of limitation.

EXAMPLE 1

Sodium hydride [0.93 grams (g); 38.8 millimole (mmol)] was charged into a fixed-bed flow reactor with vertical furnace and flushed with hydrogen carrier gas at a rate of 20 milliliters per minute (mL/min). The initial reactor temperature was about 200° C. The reactor was heated in the presence of hydrogen as carrier gas. Tetramethoxysilane [2.13 milliliters per hour (mL/h); 14.4 millimoles per hour (mmol/h)] was fed into the carrier gas stream using a motor driven syringe. The reactor effluent downstream was collected in fractions using a water-chilled condenser and analyzed by gas chromatography. Reaction was carried out with a temperature ramp. After collecting a fraction, typically in a range between about 0.5 grams and about 2 grams, the reactor temperature was increased by 25° C. or 50° C. as indicated in Table 1. The temperature was ramped for screening purposes. Low-boiling components of the reactor effluent downstream which bypassed the water chilled condenser were collected in a −78° C. cold trap. Methyltrimethoxysilane [MeSi(OMe)$_3$] formation was confirmed by gas chromatography, GC/MS and multinuclear NMR techniques. The percentages of methyltrimethoxysilane refer to percentages of the individual samples downstream of the reactor including unreacted tetramethoxysilane. Results can be seen in Table 1.

TABLE 1

| Fraction | Weight of sample (g) | Temperature (° C.) | % MeSi(OMe)$_3$ |
|---|---|---|---|
| 1 | 2.12 | 200 | 0 |
| 2 | 1.56 | 225 | 0 |
| 3 | 1.23 | 250 | 0 |
| 4 | 0.78 | 275 | 0 |
| 5 | 0.96 | 300 | 0 |
| 6 | 0.63 | 350 | 7.8 |
| 7 | 0.66 | 375 | 1.2 |

The procedure of Example 1 was followed with the following modifications: sodium hydride (1.00 g; 41.7 mmol); tetramethoxysilane (2.13 mL/h; 14.4 mmol/h); carrier gas=argon (14 mL/min). Reaction was carried out at a fixed temperature of 325° C. Results can be seen in Table 2.

TABLE 2

| Fraction | Weight of sample (g) | Temperature (° C.) | % MeSi(OMe)$_3$ |
|---|---|---|---|
| 1 | 0.69 | 325 | 6.5 |
| 2 | 1.62 | 325 | 5.0 |
| 3 | 1.74 | 325 | 6.5 |
| 4 | 1.87 | 325 | 6.4 |

EXAMPLE 3

The procedure of Example 1 was followed with the following modifications: lithium deuteride (1.82 g; 228 mmol); tetramethoxysilane (2.13 mL/h; 14.4 mmol/h); carrier gas=(14 mL/min). Reaction was carried out with a temperature ramp. After collecting a fraction, the reactor temperature was increased by either 25° C. or 50° C. as indicated in Table 3. Results can be seen in Table 3.

TABLE 3

| Fraction | Weight of sample (g) | Temperature (° C.) | % MeSi(OMe)$_3$ |
|---|---|---|---|
| 1 | 1.07 | 250 | 0 |
| 2 | 1.95 | 300 | 0 |
| 3 | 2.33 | 350 | 0.7 |
| 4 | 1.75 | 375 | 3.6 |
| 5 | 0.45 | 400 | 21.5 |

EXAMPLE 4

The procedure in Example 1 was used with the following modifications: sodium borohydride (1.04 g; 27.5 mmol); tetramethoxysilane (2.13 mL/h; 14.4 mmol/h); carrier gas= argon (14 mL/min). Reaction was carried out with a temperature ramp. After collecting a fraction, the reactor temperature was increased by 25° C. Results can be seen in Table 4.

TABLE 4

| Fraction | Weight of sample (g) | Temperature (° C.) | % MeSi(OMe)$_3$ |
|---|---|---|---|
| 1 | 0.99 | 200 | 0 |
| 2 | 1.23 | 225 | 0 |
| 3 | 2.14 | 250 | 0 |
| 4 | 1.44 | 275 | 0 |
| 5 | 0.86 | 300 | 0 |
| 6 | 1.08 | 325 | 0 |
| 7 | 1.00 | 350 | 0 |
| 8 | 1.21 | 375 | 0.5 |
| 9 | 0.93 | 400 | 2.9 |
| 10 | 0.95 | 425 | 6.3 |

EXAMPLE 5

The procedure in Example 1 was used with the following modifications: sodium hydride (95% purity, 1.00 g; 39.6 mmol); tetramethoxysilane (0.5 mL/h; 3.4 mmol/h); carrier gas=argon (1 mL/min). Reaction was carried out at a fixed temperature of 35° ?C. Results can be seen in Table 5.

TABLE 5

| Fraction | Weight of sample (g) | Temperature (° C.) | % MeSi(OMe)$_3$ |
|---|---|---|---|
| 1 | 0.94 | 350 | 24.3 |
| 2 | 1.19 | 350 | 14.5 |
| 3 | 1.30 | 350 | 3.9 |
| 4 | 1.24 | 350 | 1.3 |
| 5 | 1.75 | 350 | 0.4 |
| 6 | 0.41 | 350 | 0 |

EXAMPLE 6

The procedure in Example 1 was used with the following modifications: Sodium hydride, (95% 1.00 g; 39.6 mmol); tetraethoxysilane (0.5 mL/h; 2.2 mmol/h); carrier gas=nitrogen (1 mL/min). Results of percent ethyltriethoxysilane produced

TABLE 6

| Fraction | Weight of sample (g) | Temperature (° C.) | % MeSi(OMe)$_3$ |
|---|---|---|---|
| 1 | 1.10 | 250 | 2.1 |
| 2 | 0.92 | 300 | 1.0 |

EXAMPLE 7

The procedure in Example 1 was used with the following modifications: Sodium hydride (95% purity, 1.00 g; 39.6 mmol); tetra-n-propoxysilane (1.5 mL/h; 5.2 mmol/h); carrier gas=argon (5 mL/min). The reaction was started at 250° C. and after collection of first sample was carried out at fixed temperature (300° C.). Results of percent propyltripropoxysilane produced (PrSi(O-n-Pr)$_3$) can be seen in Table 7.

TABLE 7

| Fraction | Weight of sample (g) | Temperature (° C.) | % MeSi(OMe)$_3$ |
|---|---|---|---|
| 1 | 0.71 | 250 | 0.2 |
| 2 | 1.17 | 300 | 1.1 |

TABLE 7-continued

| Fraction | Weight of sample (g) | Temperature (° C.) | % MeSi(OMe)$_3$ |
|---|---|---|---|
| 3 | 1.33 | 300 | 2.7 |
| 4 | 0.67 | 300 | 4.4 |

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A method for the preparation of organooxysilanes containing at least one silicon-carbon bond comprising reacting at least one tetraorganooxysilane with at least one metal hydride.

2. The method according to claim 1, wherein the tetraorganooxysilane comprises tetraalkoxysilanes, tetraaryoxysilanes, tetra(alkoxyaryloxy)silanes, or combinations thereof.

3. The method according to claim 2, wherein the tetraorganooxysilane comprises tetramethoxysilane.

4. The method according to claim 2, wherein the tetraorganooxysilane comprises tetraethoxysilane.

5. The method according to claim 1, wherein the metal hydride is selected from the group consisting of sodium hydride, lithium hydride, potassium hydride, rubidium hydride, cesium hydride, magnesium hydride, calcium hydride, strontium hydride, barium hydride, aluminum hydride, sodium borohydride, lithium borohydride, potassium borohydride, and combinations thereof.

6. The method according to claim 5, wherein the metal hydride comprises sodium hydride.

7. The method according to claim 1, wherein the reaction occurs in a reactor bed which comprises a reactor selected from the group consisting of a fixed bed reactor, a fluidized bed reactor and a stirred bed reactor.

8. The method according to claim 7, wherein the reaction is operated in batch mode.

9. The method according to claim 7, wherein the reaction is operated in continuous mode.

10. The method according to claim 1, wherein the reaction is conducted at a temperature in the range between about 50° C. and about 600° C.

11. The method according to claim 10, wherein the reaction is conducted at a temperature in a range between about 200° C. and about 450° C.

12. The method according to claim 1, wherein the metal hydride is present in a mole ratio of hydride to tetraorganooxysilane in a range between about 10:1 and about 1:100.

13. The method according to claim 12, wherein the metal hydride is present in a mole ratio of hydride to tetraorganooxysilane in a range between about 5:1 and about 1:10.

14. A method for the preparation of methyltrimethoxysilane comprising reacting tetramethoxysilane with sodium hydride wherein the sodium hydride is present in a mole ratio of hydride to tetramethoxysilane in a range between about 5:1 and about 1:10.

15. A method for the preparation of ethyltriethoxysilane comprising reacting tetraethoxysilane with sodium hydride wherein the sodium hydride is present in a mole ratio of hydride to tetraethoxysilane in a range between about 5:1 and about 1:10.

* * * * *